US00PP27629P3

(12) United States Plant Patent
Bradford et al.

(10) Patent No.: US PP27,629 P3
(45) Date of Patent: Jan. 31, 2017

(54) PEACH TREE NAMED 'PEARL PRINCESS XIII'

(50) Latin Name: *Prunus persica*
Varietal Denomination: Pearl Princess XIII

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 80 days.

(21) Appl. No.: 14/544,243

(22) Filed: Dec. 15, 2014

(65) Prior Publication Data

US 2016/0174438 P1 Jun. 16, 2016

(51) Int. Cl.
*A01H 5/08* (2006.01)

(52) U.S. Cl.
USPC ..... Plt./196

(58) Field of Classification Search
USPC ..... Plt./196
See application file for complete search history.

(56) References Cited

U.S. PATENT DOCUMENTS

PP7,066 P 12/1989 Bradford
PP23,867 P3 9/2013 Bradford

*Primary Examiner* — Anne Grunberg

(57) ABSTRACT

The present invention relates to a new and distinct variety of peach tree, *Prunus persica*, broadly characterized by a medium to large size, vigorous, hardy, self-fertile, productive and regular bearing tree. The variety blooms during the late season and requires about 650 chilling hours. The fruit matures under the ecological conditions described in the last half of August, with first picking on Aug. 19, 2014. The fruit is uniform, large in size, globose to oblate in shape, freestone in type, firm in texture, pale yellow green in flesh color, nearly full red in skin color, and mildly sub-acidic in flavor with 17 brix typical.

1 Drawing Sheet

Botanical classification: *Prunus persica.*
Variety denomination: 'PEARL PRINCESS XIII'.

BACKGROUND OF THE VARIETY

In a continuing effort to improve the quality of shipping fruits, we, the inventors, typically hybridize a large number of peach, nectarine, plum, apricot, and cherry seedlings each year. We also grow a smaller number of open pollinated seeds of each of these fruits, usually to capture recessive traits. The present invention relates to a new and distinct variety of peach tree, which has been denominated varietally as 'Pearl Princess XIII'.

The present variety was hybridized by us in 2004 as a first generation cross using 'Diamond Princess' (U.S. Plant Pat. No. 7,066) peach as the selected seed parent and an unnamed white flesh peach (unpatented) as the selected pollen parent. The fruit of this cross was gathered that summer, and the seeds were removed, cracked, stratified, germinated, and grown as seedlings on their own root in our greenhouse. Upon reaching dormancy the seedlings were transplanted as a group to a cultivated area of our experimental orchard located near Le Grand, Calif., in Merced County (San Joaquin Valley). During the fruit evaluation season of 2008 we selected the present variety as a single tree from the group of seedlings described above. Subsequent to origination of the present variety of peach tree, we asexually reproduced it by budding and grafting in the experimental orchard described above, and such reproductions were true to the original tree in all respects. The reproduction of the variety included the use of 'Nemaguard' (unpatented) rootstock upon which the present variety was compatible and true to type.

The present variety is similar to its seed parent, 'Diamond Princess' (U.S. Plant Pat. No. 7,066) peach by having a vigorous tree, by being self-fertile, by having showy blossoms that bloom in the late season, and by producing freestone peaches that are firm and mostly red in skin color, but is quite distinguished therefrom by having globose instead of reniform leaf glands and by producing fruit that is white instead of yellow in flesh color and that mature about sixty days later.

The present variety is most similar to 'Glacier Princess' (U.S. Plant Pat. No. 23,867) peach by being self-fertile and productive, by having showy flowers, and by producing peaches that are freestone in type, mostly red in skin color, white in flesh color, large in size, firm in texture, and good in flavor, but is distinguished by having a larger and more vigorous tree, by having globose instead of reniform leaf glands, by blooming about fourteen days later, by requiring more chilling hours, and by producing fruit that is lower in acid and that matures about eight days earlier.

The present variety is similar to its pollen parent (unnamed and unpatented) by being self-fertile and productive, by having showy flowers, and by producing peaches that are freestone in type, mostly red in skin color, white in flesh color, and good in flavor, but is distinguished by producing fruit that is larger in size, that is firmer in texture, and that matures about 20 days earlier.

SUMMARY OF VARIETY

In summary, the present peach tree variety is characterized by a medium to large size, vigorous, hardy, self-fertile, productive and regular bearing tree. The variety blooms during the late season and requires about 650 chilling hours. The fruit matures under the ecological conditions described in the last half of August, with first picking on Aug. 19, 2014. The fruit is uniform, large in size, globose to oblate in shape, freestone in type, firm in texture, white in flesh color, nearly full red in skin color, and mildly sub-acidic in flavor with 17 brix typical.

DRAWING

The accompanying photograph consists of four whole fruits positioned to display the characteristics of the skin color and form, one divided fruit to reveal the flesh and stone, two insets to reveal buds and blossoms, and typical leaves.

POMOLOGICAL CHARACTERISTICS

Referring now more specifically to the pomological characteristics of this new and distinct variety of peach tree, the following has been observed under the ecological conditions prevailing near Le Grand, Merced County (San Joaquin Valley), Calif., and was developed at the state of firm ripe on Aug. 24, 2014, on the original tree during its tenth growing season. The blossom and flower descriptions were made the previous blooming season. All major color code designations are by reference to the Inter-Society Color Council, National Bureau of Standards. Common color names are also used occasionally.

It is to be noted that 2014 was an abnormal year with drought conditions existing in California. The unusually clear, warm, and dry weather in January led to a very low amount of acquired chilling units, an earlier than normal blooming season, and an earlier than normal ripening season for the entire spring and summer.

PARENTAGE

Seed parent: 'Diamond Princess' (U.S. Plant Pat. No. 7,066) peach.

Pollen parent: Unnamed peach (unpatented).

TREE

Size: Medium to large, reaching and maintaining a height of 12' [3.66 m.] and a spread of 10' [3.05 m.] after ten growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Upright and spreading.

Form: Vase formed.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning necessary.

Fertility: Self-fertile.

Bearing: Regular bearer with no alternate bearing yet observed.

Approximate chilling requirement: 650 hours.

Trunk:

*Size.*—Medium, reaching a maximum diameter of 5½" [139.7 mm.] after the tenth growing season.

*Texture.*—Medium shaggy.

*Bark color.*—A Grayish brown [61. gy.Br] and Darkish grayish yellowish brown [81. d.gy.yBr] variegation with Dark grayish reddish brown [47. d.gy.rBr] crevices present.

*Lenticels.*—Approximate Number Per Square Inch: 10. Color: Moderate orange [53. m.O]. Size: ⅛" [3.2 mm.] to ⅜" [9.5 mm.] in length. Width is typically one fourth as much as the length. Shape: Eye-shaped, elongated.

Branches:

*Size.*—Medium, diameter of main scaffold is 3¼" [82.6 mm.] measured 12" above the crotch, diameter of limb is 2¼" [57.2 mm.] measured 12" above the first fork.

*Texture.*—Medium shaggy.

*Color.*—1st Year Wood Topside: Grayish red [19. gy.R]. 1st Year Wood Underside: Brilliant yellow green [116. brill.YG]. 2nd Year and Older Wood: Strong yellowish brown [74. s.yBr].

*Lenticels.*—Number Per Square Inch: About 120 on second year wood. Color: Moderate orange yellow [71. m.OY]. Size: Small, 1/64" [0.4 mm.] to 1/16" [1.6 mm.] in length on second year wood. Width is typically one fourth as much as the length. Shape: Rectangular, elongated.

Leaves:

*Size.*—Large. Average Length: 6¼" [158.8 mm.]. Average Width: 1⅝" [41.3 mm.].

*Arrangement.*—Alternate.

*Thickness.*—Medium.

*Form.*—Elliptical.

*Apex.*—Acuminate.

*Base.*—Acute, average angle of 75°.

*Surface.*—Smooth.

*Color.*—Dorsal Surface: Moderate olive green [125. m.OlG]. Ventral Surface: Moderate yellow green [120. m.YG].

*Margin.*—Finely serrate.

*Venation.*—Pinnately net veined.

*Vein color.*—Light yellow green [119. l.YG].

*Petiole.*—Average Length: ½" [12.7 mm.]. Average Thickness: 1/16" [1.6 mm.]. Color: Brilliant yellow green [116. brill.YG].

*Stipules.*—Number: 2 per leaf, up to 6 per growing tip. Average Length: ¼" [6.4 mm.]. Color: Brilliant yellow green [116. brill.YG]. Surface: Smooth.

*Glands.*—Number: Mostly 2 per leaf. Position: Oppositely positioned on the petiole near the base of leaf blade. Size: Medium, about 1/48" [0.5 mm.] in diameter. Form: Globose. Color: Strong yellow green [117. s.YG] acquiring a Grayish brown [61. gy.Br] center with age.

*Leaf buds.*—Pointed, medium in size.

*Limbs.*—Color: First year wood topside: Grayish red [19. gy.R]. First year wood underside: Strong yellow green [117. s.YG].

Flower buds:

*Hardiness.*—Hardy, with respect to central California winters.

*Diameter.*—Typically ⅜" [9.5 mm.] 1 week before bloom.

*Length.*—Typically ¾" [19.1 mm.] 1 week before bloom.
*Form.*—Not appressed.
*Surface.*—Pubescent.
*Tip color.*—Light purplish pink [249. l.pPk].

Flowers: Perfect, complete, perigynous, usually a single pistil, about thirty stamens, five sepal and petal locations alternately positioned.
*Type.*—Showy, large.
*Average flower diameter.*—2 1/16" [52.4 mm.].
*Average flower depth.*—⅝" [15.9 mm.] when fully open.
*Number of petals.*—Always five full petals with about ten percent having extra petals or petal fragments, full double blossoms not observed.
*Petal shape.*—Circular to oval.
*Petal margin.*—Entire, somewhat wavy with very few notches.
*Average petal diameter.*—¾" [19.1 mm.].
*Average petal length.*—13/16" [20.6 mm.].
*Petal apex.*—Rounded.
*Petal base.*—Rounded.
*Petal color.*—Light pink [4. l.Pk] toward the apex, Pale pink [7. p.Pk] toward the base on both sides.
*Stamen position.*—Typically located about 1/32" [0.8 mm] below the petals.
*Anther color.*—Dark red [16. d.R] over a Light yellow [86. l.Y] center at bloom onset.
*Pollen.*—Anthers produce an abundance of Brilliant yellow [83. brill.Y] pollen.
*Stigma color.*—Pale greenish yellow [104. p.gY].
*Stigma position.*—Typically located about 1/16" [1.6 mm.] below the nearby anthers.
*Ovary.*—Pubescent.
*Sepal color.*—Dark purplish red [259. d.pR] on the outer surface. The inner surface is somewhat translucent Pinkish white [9. pkWhite] with both Grayish purplish red [262. gy.pR] and Vivid yellow green [115. v.YG] areas visible.
*Sepal length.*—5/16" [7.9 mm.].
*Sepal width.*—¼" [6.4 mm.].
*Sepal apex.*—Rounded to elliptical to match the sepal length and width.
*Sepal margin.*—Fairly smooth.
*Average pistil length.*—⅝" [15.9 mm.].
*Average stamen length.*—9/16" [14.3 mm.].
*Fragrance.*—Moderate.
*Blooming period.*—Late season, blooms about two days before 'Diamond Princess' (U.S. Plant Pat. No. 7,066) peach.
*Onset of bloom.*—One percent on Feb. 28, 2014.
*Date of full bloom.*—Mar. 8, 2014.
*Duration of bloom.*—One to two weeks, dependent on ambient temperature.
*Number per cluster.*—1 to 3 with single flowers most common.

FRUIT

Maturity when described: Firm ripe, Aug. 24, 2014.
Date of first picking: Aug. 19, 2014.
Date of last picking: Aug. 28, 2014.

Size: Uniform, large.
*Average diameter axially.*—3" [76.2 mm.].
*Average diameter across suture plane.*—3 7/16" [87.3 mm.].
*Average diameter across cheek plane.*—3⅜" [85.7 mm.]
*Typical weight.*—12.8 ounces [363 grams].

Form: Uniform, globose to slightly oblate, compressed axially, mostly symmetrical.
*Longitudinal section form.*—Round to oblate.
*Axial view.*—Round.

Suture: A distinct line extending from the stem and terminating with a slight depression just past the pistil point.
*Near the base.*—A sharp groove.
*Along the side.*—A distinct line with occasional stitching.
*Near the apex.*—A very shallow groove.

Ventral surface: Rounded.

Lips: Equally lipped very slightly toward the apex, with almost no lipping on the side.

Cavity: Flaring, circular to somewhat elongated in the suture plane, suture showing on one side, Yellowish white [92. yWhite] stem markings typical.
*Depth.*—⅝" [15.9 mm.].
*Breadth.*—1⅜" [34.9 mm.].

Base: Somewhat truncate.

Apex: Rounded to slightly truncate.

Pistil point: Negligible in length, some apical and some oblique, usually depressed within the suture.

Stem: Medium.
*Average length.*—⅜" [9.5 mm.].
*Average width.*—3/16" [4.8 mm.].

Skin:
*Thickness.*—Medium.
*Surface.*—Pubescent.
*Down.*—Scant, short, does not roll up when rubbed.
*Tenacity.*—Tenacious to flesh.
*Astringency.*—Non-astringent.
*Tendency to crack.*—None observed in dry season.
*Color.*—Dark red [16. d.R] smoothly blending into a Moderate pink [5. m.Pk] background.

Flesh:
*Color.*—White [263. White] with Dark red [16. d.R] streaking next to the stone.
*Surface of pit cavity.*—Covered with Dark pink [6. d.Pk] to Dark red [16. d.R] fibers.
*Amygdalin.*—Scarce.
*Juice.*—Moderate, rich.
*Texture.*—Genetically melting, but remains firm and crisp through the harvest period.
*Fibers.*—Abundant, fine, tender.
*Ripens.*—Fairly even.
*Flavor.*—A mild sub-acid, average of 17 Brix.
*Aroma.*—Very slight.
*Eating quality.*—Good.

STONE

Type: Freestone.
Form: Oval.
Hilum: Narrow, oblong.
Base: Truncate, slightly oblique.
Apex: Acuminate, with a sharp tip of length ⅛" [3.2 mm.].
Sides: Equal.

Surface: Irregularly furrowed near the apex, pitted toward the base.
Ridges: Jagged.
External color: Deep brown [56. deep Br].
Pit wall color when cracked: Moderate brown [58. m.Br].
Cavity surface color: Strong yellowish brown [74. s.yBr].
Average pit wall thickness: ¼" [6.4 mm.].
Average width: 1⅛" [28.6 mm.].
Average length: 1½" [38.1 mm.].
Average breadth: ⅞" [22.2 mm.].
Tendency to split: None observed.
Kernel:
*Form.*—Oval.
*Skin color.*—Strong yellowish brown [74. s.yBr] when first removed.
*Pellicle color.*—Deep brown [56. deep Br].
*Vein color.*—Moderate brown [58. m.Br].
*Taste.*—Bitter.
*Viable.*—Yes.
*Average width.*—½" [12.7 mm.].
*Average length.*—⅞" [22.2 mm.].
*Amygdalin.*—Moderate.

Use

Market: Fresh market and long distance shipping.
Keeping quality: Good, fruit quality observed to remain in good condition after 17 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of peach tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of peach tree, substantially as illustrated and described, that is most similar to 'Glacier Princess' (U.S. Plant Pat. No. 23,867) peach by being self-fertile and productive, by having showy flowers, and by producing peaches that are freestone in type, mostly red in skin color, white in flesh color, large in size, firm in texture, and good in flavor, but is distinguished by having a larger and more vigorous tree, by having globose instead of reniform leaf glands, by blooming about fourteen days later, by requiring more chilling hours, and by producing fruit that is lower in acid and that matures about eight days earlier.

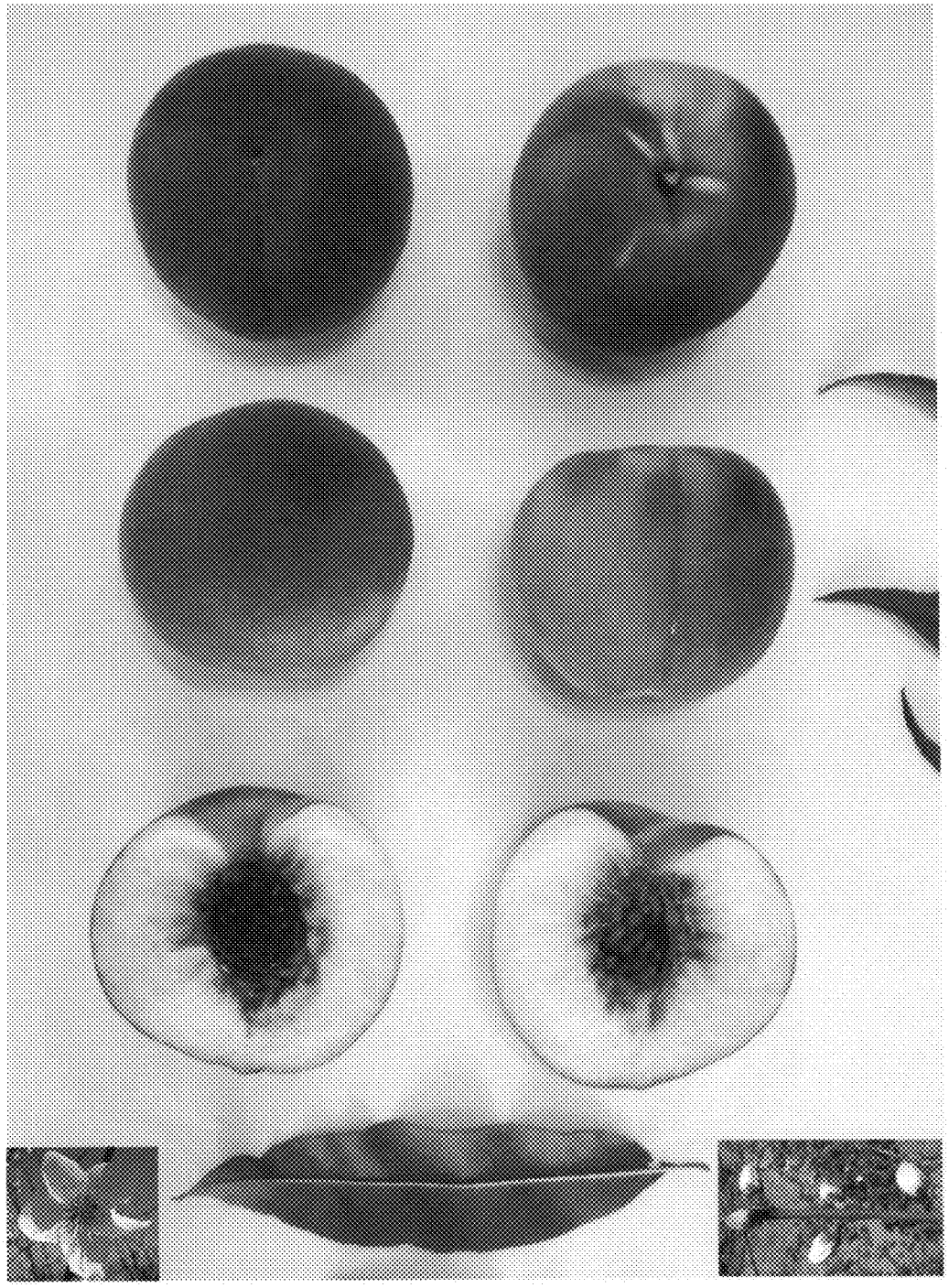

* * * * *